United States Patent
Fu et al.

(10) Patent No.: US 7,118,987 B2
(45) Date of Patent: Oct. 10, 2006

(54) METHOD OF ACHIEVING IMPROVED STI GAP FILL WITH REDUCED STRESS

(75) Inventors: Chu-Yun Fu, Taipei (TW); Chih-Cheng Lu, Taipei (TW); Syun-Ming Jang, Hsin-Chu (TW)

(73) Assignee: Taiwan Semiconductor Manufacturing Co., Ltd., Hsin Chu (TW)

( * ) Notice: Subject to any disclaimer, the term of this patent is extended or adjusted under 35 U.S.C. 154(b) by 0 days.

(21) Appl. No.: 10/767,657

(22) Filed: Jan. 29, 2004

(65) Prior Publication Data

US 2005/0170606 A1   Aug. 4, 2005

(51) Int. Cl.
   *H01L 21/76* (2006.01)
(52) U.S. Cl. .............. 438/435; 438/436; 438/437; 257/637; 257/639; 257/640
(58) Field of Classification Search ........ 438/435–438; 257/635, 637, 639–642, 644
See application file for complete search history.

(56) References Cited

U.S. PATENT DOCUMENTS

| | | | |
|---|---|---|---|
| 6,242,323 B1 * | 6/2001 | Ishitsuka et al. ............ 438/435 |
| 6,261,920 B1 * | 7/2001 | Oyamatsu .................... 438/424 |
| 6,461,937 B1 * | 10/2002 | Kim et al. ................... 438/431 |
| 6,566,229 B1 * | 5/2003 | Hong et al. ................. 438/435 |
| 6,596,607 B1 * | 7/2003 | Ahn ........................... 438/424 |
| 6,683,354 B1 * | 1/2004 | Heo et al. ................... 257/397 |
| 6,693,050 B1 * | 2/2004 | Cui et al. ................... 438/782 |

* cited by examiner

Primary Examiner—Zandra V. Smith
Assistant Examiner—Christy Novacek
(74) Attorney, Agent, or Firm—Tung & Associates

(57) ABSTRACT

A shallow trench isolation (STI) structure and method of forming the same with reduced stress to improve charge mobility the method including providing a semiconductor substrate comprising at least one patterned hardmask layer overlying the semiconductor substrate; dry etching a trench in the semiconductor substrate according to the at least one patterned hardmask layer; forming one or more liner layers to line the trench selected from the group consisting of silicon dioxide, silicon nitride, and silicon oxynitride; forming one or more layers of trench filling material comprising silicon dioxide to backfill the trench; carrying out at least one thermal annealing step to relax accumulated stress in the trench filling material; carrying out at least one of a CMP and dry etch process to remove excess trench filling material above the trench level; and, removing the at least one patterned hardmask layer.

24 Claims, 4 Drawing Sheets

US 7,118,987 B2

METHOD OF ACHIEVING IMPROVED STI GAP FILL WITH REDUCED STRESS

FIELD OF THE INVENTION

This invention generally relates to integrated circuit manufacturing processes and more particularly to an improved shallow trench isolation (STI) formation process and structure to form a STI feature with improved gap filling with reduced stress thereby improving charge carrier mobility.

BACKGROUND OF THE INVENTION

As devices become smaller and integration density increases, high density plasma chemical vapor deposition (HDP-CVD) has become a key process due in back filling high aspect ratio features such as shallow trench isolation (STI) features due to its superior gap-filling capability. In particular, high density plasma (HDP) processes, such as electron cyclotron resonance (ECR) processes and inductively coupled plasma (ICP) processes have been found to produce high-quality field oxides. Generally, HDP-CVD provides a high density of low energy ions resulting in higher quality films at lower deposition temperatures, compared to other plasma enhanced CVD deposition processes such as PECVD.

In a HDP-CVD deposition process, for example, a bias power is coupled to the semiconductor wafer to attract ions which sputter (etch) the wafer during deposition (re-sputtering effect), thereby preventing a phenomenon known as crowning where the deposition material converges over the trench before an etched feature opening is completely filled with the deposition material. The deposition rate may therefore be more finely tuned to improved CVD deposition properties to, for example, avoid crowning.

As device sizes decrease below 0.13 micron critical dimension, however, the gap fill of openings, for example STI openings, becomes problematical and the process window for successful gap filling is narrowed. Generally, as device sizes decrease and aspect ratios increase to greater than about 4 to 1, relatively high plasma RF powers, for example, greater than about 6 Watts/cm$^2$ are delivered to a process water surface creating relatively large thermal stresses during the gap filling desposition. To maintain lower deposition temperatures the backside of the water is frequently cooled, leading to increased thermal gradients and consequently stresses across the wafer surface and through the wafer thickness. Consequently, compressive stresses, relatively larger parallel to the wafer process surface, are generated following the HDP-CVD process loading to subsequent problems in device quality and reliability. For example, charge carrier mobilities are strongly influenced, e.g., decreased due to stresses fields present in semiconductor materials.

There is therefore a need in the integrated circuit manufacturing art to develop an improved method for filling gaps including shallow trench isolation (STI) structures as well as a STI structure having reduced stresses to achieve improved semiconductor device quality and reliability.

It is therefore among the objects of the present invention to improved an improved method for filling gaps including shallow trench isolation (STI) structures as well as forming a STI structure having reduced stresses to achieve improved semiconductor device quality and reliability, in addition to overcoming other shortcomings and deficiencies of the prior art.

SUMMARY OF THE INVENTION

To achieve the foregoing and other objects, and in accordance with the purposes of the present invention, as embodied and broadly described herein, the present invention provides a shallow trench isolation (STI) structure and method of forming the same with reduced stress to improve CMOS device charge mobility.

In a first embodiment, the method includes providing a semiconductor substrate comprising at least one patterned hardmask layer overlying the semiconductor substrate; dry etching a trench in the semiconductor substrate according to the at least one patterned hardmask layer; forming one or more liner layers to line the trench selected from the group consisting of silicon dioxide, silicon nitride, and silicon oxynitride; forming one or more layers of trench filling material comprising silicon dioxide to backfill the trench; carrying out at least one thermal annealing step to relax accumulated stress in the trench filling material; carrying out at least one of a CMP and dry etch process to remove excess trench filling material above the trench level; and, removing the at least one patterned hardmask layer.

These and other embodiments, aspects and features of the invention will be better understood from a detailed description of the preferred embodiments of the invention which are further described below in conjunction with the accompanying Figures.

DETAILED DESCRIPTION OF THE PREFERRED EMBODIMENTS

According to the present invention a method for improved gap fill is explained with reference to the formation of an exemplary shallow trench isolation (STI) feature and exemplary CMOS device. While the method of the present invention is particularly advantageously applied to the formation of STI features, it will be appreciated that the method of the present invention may be applied to the filling of other types of gaps or openings in an integrated circuit manufacturing process where reduced stresses may advantageously improve charge mobility.

Figure 1A:
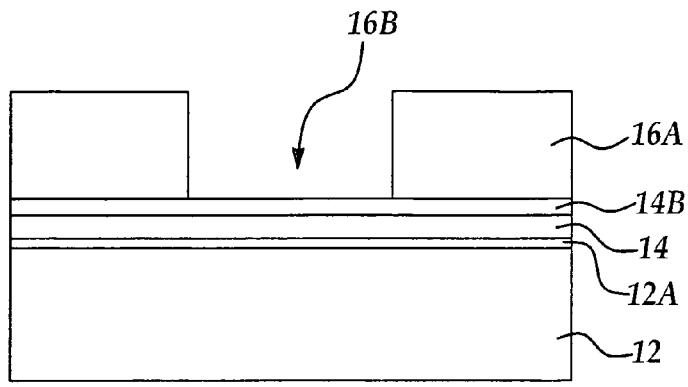
FIGS. 1A–1F are representational cross sectional side views of a portion of a semiconductor device including a STI feature at stages in manufacturing according to an embodiment of the present invention.

In one exemplary implementation of the present invention, referring to FIG. 1A is shown a semiconductor substrate 12, for example single crystalline or polycrystalline silicon. It will be appreciated that the substrate may include epi silicon layer, buried layers, silicon on insulator (SOI), SiGe, and GaAs. A pad oxide layer 12A of SiO$_2$ about 50 Angstroms to about 150 Angstroms is first thermally grown by conventional processes or formed by LPCVD TEOS over the silicon substrate 12 to aid in reducing surface stresses induced in subsequent processing steps. A silicon nitride (e.g., $Si_3N_4$) layer 14 is then deposited by a CVD method, for example, LPCVD, to a thickness of about 500 Angstroms to about 2000 Angstroms.

A second hardmask layer 14B may optionally be added as a hardmask for a subsequent dry etch process, for example formed of PECVD SiON, PECVD $SiO_2$, or LPCVD TEOS. The second hardmask layer 14B may be formed over the SiN layer 14 to a thickness of about 150 Angstroms to about 500 Angstroms. In addition, an organic or inorganic anti-reflective coating (ARC) is preferably formed over the SiN hardmask or second hardmask, if present, to a thickness of about 200 Angstroms to about 1000 Angstroms, depending on the wavelength of light to be used in the photolithographic process. For example, a second hardmask formed of SION may be deposited to a thickness between about 500 Angstroms and about 1000 Angstroms to function as both an etching hardmask and as an ARC layer.

Still referring to FIG. 1A, a photoresist layer 16A, e.g., 1000 to 6000 Angstroms thick is then deposited over the second hardmask/ARC layer 14B and photolithographically patterned to form an opening e.g., 16B exposing a portion of the second hardmask/ARC layer 14B for dry etching through a thickness portion of the second and SiN hardmask layers, e.g., 14B and 14 respectively, to form a dry etching hardmask.

Figure 1B:
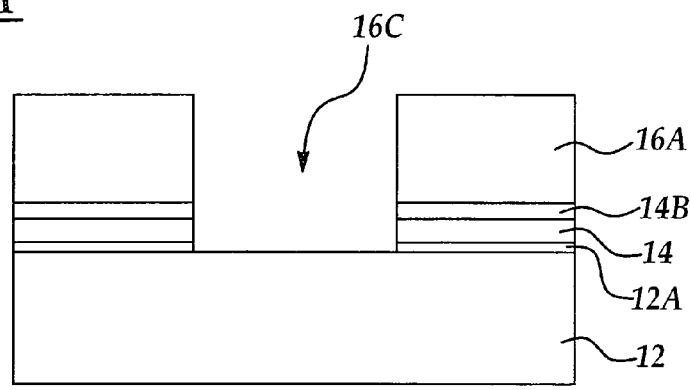

Referring to FIG. 1B, the hardmask/ARC layer 14B and SiN hardmask layer 14 are then etched according to the patterned photoresist layer opening 16B by conventional process to expose a portion of the substrate 12 to form hardmask opening 16C according to a conventional reactive ion etch (RIE) process, for example including a fluorocarbon etching chemistry, for example, $CF_4$. For example, the silicon nitride hardmask layer 14 is anisotropically dry etched through a thickness to include the pad oxide layer 12A to expose a surface portion of the substrate 12 according to endpoint detection.

Figure 1C:
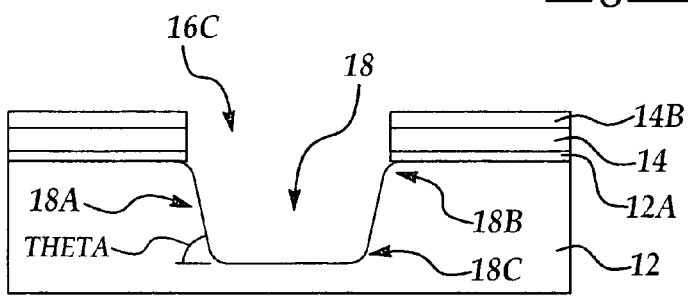

Referring to FIG. 1C, in one aspect of the method of the present invention, following removal of the photoresist layer 16A, for example, by a wet stripping or dry ashing process, a STI trench feature 18 is then dry etched into the silicon substrate to a depth between about 60 Angstroms and about 5000 Angstroms, preferably forming sloped sidewall portions, e.g., 18A having an angle, theta, with respect to the plane of the major surface (process surface) of the substrate preferably between about 80 and 89 degrees, the upper portion of the trench being wider than the bottom portion. A conventional etching chemistry, including for example, $Cl_2$, HBR, and $O_2$ is used to dry etch the trench 18 unto the substrate 12 to from a shallow trench isolation (STI) opening (trench opening) 18. Preferably, during the trench etching process, trench top portion corners at e.g., 18B and trench bottom portion corners e.g., 18C are formed such that that the trench opening corners at the top and/or bottom corner portions of the trench are rounded e.g., having a radius of curvature. Such STI trench corner rounding is advantageous for preventing undesirable electrical behavior such as high electrical fields affecting voltage threshold ($V_T$) in a completed CMOS device.

For example, several STI trenches are etched simultaneously in a semiconductor substrate, being spaced between about 0.06 microns and about 0.30 microns, each STI trench and having an upper portion wider than a lower portion, the upper portion width between about 0.03 microns and about 0.20 microns.

Figure 1D:
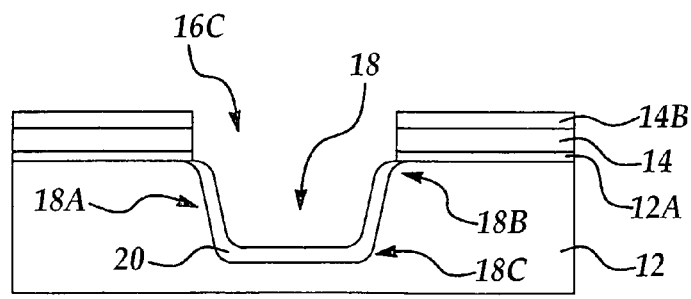

Referring to FIG. 1D following etching of the trench 18, a conventional cleaning process using SC-1 and SC-2 cleaning solutions is carried out to clean the substrate surface including exposed portions in the STI trench. In another aspect of the invention, one or more layers e.g., 20 are deposited to line the trench opening. For example in one embodiment, the one or more liner layers including at least one of thermal oxide ($SiO_2$), silicon nitride (e.g., SiN, $Si_3N_4$), and silicon oxynitride (e.g., SiON), including for example, one of an $SiO_2$/SiN, $SiO_2$/SiON, $SiO_2$/SiN/SiON, and $SiO_2$/SiON/SiN stack having a total thickness of about 30 to about 200 Angstroms. For example, in the case of a silicon substrate, a single layer of thermal oxide may be grown by conventional thermal processes over silicon exposed portions of the trench 18 to form a substantially conformal layer of about 30 Angstroms to about 200 Angstroms in thickness. For example, the thermal oxide is grown at a temperature of about 900° C. to about 1150° C. in a conventional furnace or RTP apparatus. In one embodiment, the thermal oxide layer is treated with $N_2$ to form an uppermost layer of SiN, for example by treating the thermal oxide in ambient $N_2$ at a temperature of from about 800° C. to about 1000° C., or carrying out a nitrogen atom implant process, e.g., plasma immersion or ion implantation, followed by annealing at greater than about 600° C.

In another embodiment, an LPCVD, PECVD, or ALCVD process is carried to blanket deposit a silicon nitride or silicon oxynitride layer over a thermal oxide to form the trench liner 20. Alternatively, trench liner 20 may be formed of single or multiple layers of SiN and SiON which are deposited without first forming the thermal oxide. However, forming the thermal oxide is preferred in the case a silicon substrate is used, since it tends to better repair any damage caused by etching and to relax thermally induced stresses at the trench surface. In the case, the substrate is not silicon, for example GaAs, the oxide layer may be formed by LPCVD or ALCVD over the exposed substrate portions within the STI trench, prior to forming SiN and/or SiON overlayers. For example, SiN is preferably formed by a LPCVD, PECVD, or ALCVD process by reacting silane (SiH4) and $NH_3$ at about 400° C. to about 800° C. Silicon oxynitride (e.g., SiON) is preferably formed by reacting silane (SiH4), $NH_3$, oxygen ($O_2$) and/or $N_2O$ at deposition temperatures of about 350° C. to about 800° C.

In one embodiment the trench liner is formed of a triple layer of $SiO_2$/SiN/SiON or $SiO_2$/SiON/SiN, for example by a first oxide formation process, e.g., thermal growth, ALCVD, ALCVD, followed by an LPCVD, PECVD, or ALCVD, preferably an LPCVD or ALCVD process to deposit SiN and/or SiON. It will be appreciated that the term SiN is intended to include the various stoichiometries of silicon nitride, e.g., $Si_xN_y$, including $Si_3N_4$. In addition, the term SiON is intended to include the various stoichiometries of silicon oxynitride e.g., $Si_xO_yN_z$. Following the formation of the trench liner 20, preferably a thermal annealing process is carried out to relax thermally induced stresses formed by previous trench liner 20 formation processes, for example using a furnace or RTP process at 500° C. to 1100° C. in either ambient $O_2$ or $N_2$.

According to another aspect of the invention, one or more layers of $SiO_2$ are blanket deposited to backfill the trench to produce a reduced stress trench filling material compared to conventional HDP-CVD methods. Preferably the trench filling material layers are formed of undoped silicate glass (USG) and/or SOG. Preferably the USG is formed by reacting tetraethylorthosilicate (TEOS) and ozone ($O_3$) or silane ($SiH_4$) and $O_2$. Preferably, the USG deposition process includes sub-atmospheric pressure CVD (SACVD), atmospheric pressure CVD (APCVD), and/or high density plasma CVD (HDPCVD) at a deposition temperature from about 400° C. to about 800° C. The SOG may be organic or inorganic spin on glass (SOG) e.g., preferably including siloxane or silicate precursors, respectively. Preferably, the SOG precursor comprises flowable mixtures including cross-linking agents to form cross-linked polymers, followed by a curing process at about 350° C. to about 450° C. to form cross-linked SiO and/or $SiO_2$ groups. Alternatively, polysesilquioxanes may be used followed by a curing process of about 100° C. to about 175° C.

Figure 2A:
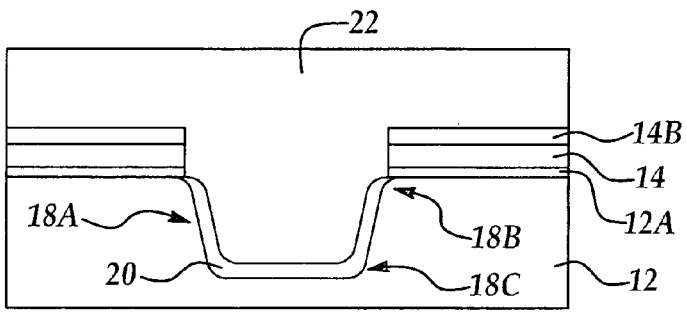
FIGS. 2A–2C are representational cross sectional side views of a portion of a semiconductor device including a STI structure formed according to exemplary embodiments of the present invention.

Referring to FIG. 2A, in one embodiment of the present invention, the STI trench 18 is backfilled completely with a single layer 22 of one of an organic or inorganic SOG (following curing), or SACVD or APCVD USG. In an important aspect of the invention, an annealing process is then carried out at a temperature of about 500° C. to about 1100° C. to relieve any stresses created by the deposition process. Preferably, the annealing process is carried out in an ambient $O_2$ and/or $N_2$ containing atmosphere for 10 seconds to about 3 hours in a furnace for treating multiple wafers or RTP (rapid thermal process) apparatus for treating single wafers as is known in the art. In addition, a low compressive stress HDP-CVD process may be used to deposit USG followed by the stress reducing annealing process according to preferred embodiments to form a stress relaxed STI structure.

Figure 2B:
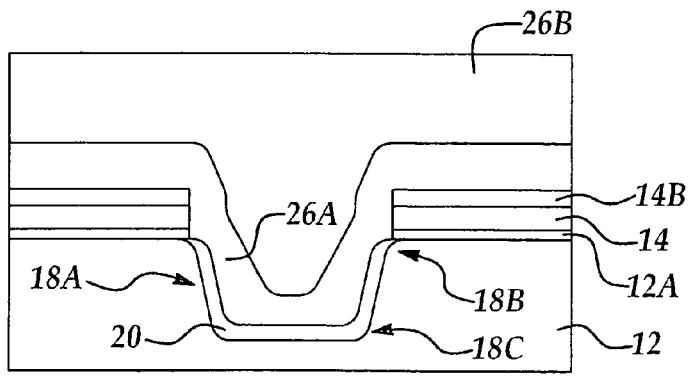

Referring to FIG. 2B, in another embodiment, multiple layers of $SiO_2$ are deposited to backfill the STI trench. For example, a first layer 26A of SOG is deposited by a spin on process followed by a curing process to fill the STI trench to less than or equal to half the STI trench depth. A USG layer, e.g., 26B is then deposited using TEOS and $O_3$ or $SiH_4$ and $O_2$ by an SACVD, APCVD, or HDPCVD process at about 400° C. to about 800° C. Advantageously, during the CVD process residual stresses formed by the SOG layer 26A during the curing and shrinking process are released. Preferably, in an important aspect of the invention, following the CVD process, an additional annealing process is carried out at a temperature of about 500 to about 1100° C. to further relieve any stresses in the deposited $SOG/SiO_2$ layers. It will be appreciated that the order of depositing the layers may be reversed, however is less preferred due to the tendency of the SOG to absorb moisture.

Figure 2C:
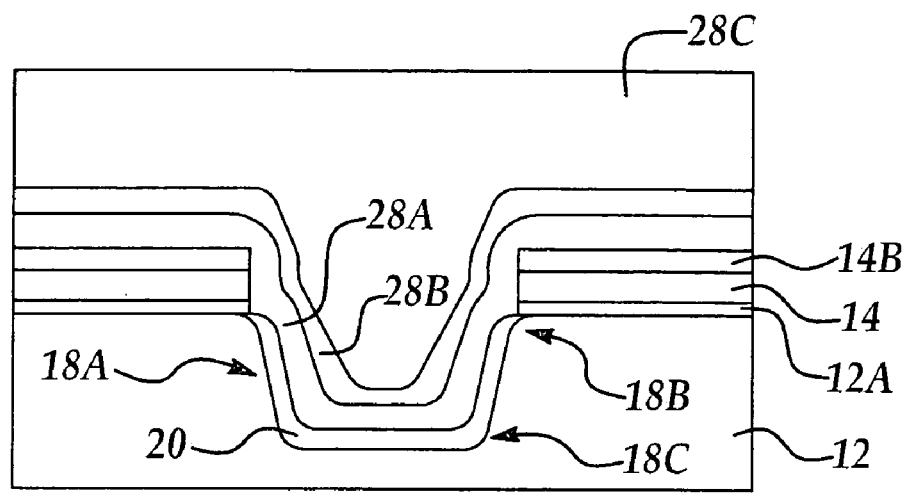

Referring to FIG. 2C, in another embodiment, a plurality of trench filling layers are formed with one or more CVD USC layers, e.g., SACVD, APCVD, or HDPCVD, together with one or more SOC layers, with an optional annealing process performed between each layer deposition, but at least following deposition of the uppermost trench filling layer. For example, a first layer 28A of CVD USG or SOG (including a curing process) is deposited to about less than about ½, e.g. about ⅓ the depth of the trench by a first deposition using a CVD process or SOG process (including a curing process) followed by an annealing process according to preferred embodiments. A second layer 28B of CVD USG or SOG (including a curing process is then deposited to about the same thickness followed by a second annealing process. A third layer e.g., 28C of CVD USG or SOG (including a curing process) is then deposited to a final thickness e.g., the deposited layers having a total thickness of from about 2000 to about 8000 Angstroms, followed by a third annealing process. Preferably, a HDP-CVD process is used for only the second and subsequent deposited layers e.g., 28B, 28C layers of SOG or APCVD or SACVD, to reduce the possibility of void formation. In addition, with multiple layers being formed of SOG oxide, SACVD oxide (USG) and/or APCVD oxide (USG), an annealing process between layer depositions may be optionally foregone, with the annealing process carried out following deposition of the final oxide layer.

Still referring to FIG. 2C, in another embodiment, the initial layer e.g., first layer 28A of CVD USG is deposited to fill less than about ½ the depth, e.g., about ⅓ of the STI trench using e.g., SACVD, APCVD or HDP-CVD, followed by an optional-annealing process according to preferred embodiments. The second layer, e.g., layer 28B, is formed of SOG formed to about the same or greater thickness following a curing process. The third layer, e.g., 28C of CVD USG is then deposited to form the final thickness by e.g., e.g., SACVD, APCVD or HDP-CVD, followed by an annealing process according to preferred embodiments.

Figure 2D:
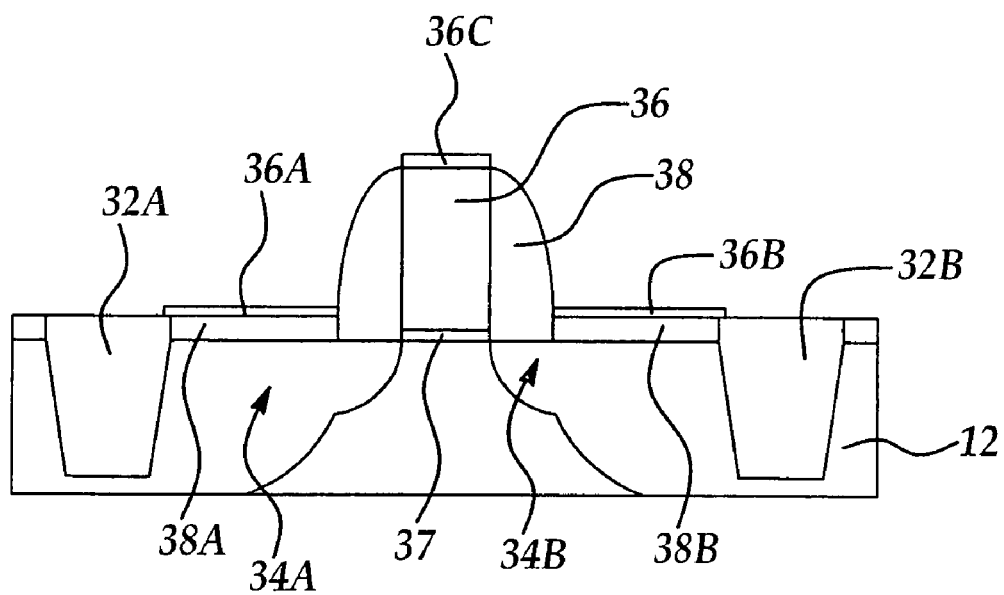
FIG. 2D is a completed CMOS device including STI structures formed according to embodiments of the present invention.

According to preferred embodiments for forming a reduced (relaxed) stress STI oxide filling, it has been found that MOSFET device performance is improved. For example, by reducing stresses in the length and width directions of the STI oxide, e.g., In the plane of (parallel) or perpendicular to the semiconductor substrate major surface, charge carrier mobility, including electrons and holes in N and PMOS devices, respectively, is improved in adjacent semiconductor material portions. The improvement in charge carrier mobility shows improvement particularly in the case of subsequent formation of self aligned metal silicides (salicides), e.g., $CoSi_2$, NiSi, and $TiSi_2$, over source/drain regions of the semiconductor substrate, including e.g., silicon epitaxially grown (SEG) raised source/drain regions. For example referring to FIG. 2D is shown an exemplary MOSFET device having STI regions 32A and 32B formed according to preferred embodiments in semiconductor substrate 12, followed by conventional processes to form S/D doped regions e.g., 34A, a polysilicon gate structure 36 with gate oxide 37, oxide and/or nitride spacers e.g., 38, SDE doped regions 34B, and salicide regions e.g., 36A, 36B, formed over raised S/D silicon epitaxial growth (SEG) regions e.g., 38A and 38B, as well as an upper portion of the polysilicon gate structure, e.g. 36C. The improved charge carrier mobility in the S/D regions adjacent the relaxed oxide filled STI structures 32A and 32B, for example, reduces sheet resistance, allowing shallower junction depths (e.g., SDE regions) to be formed, including raised S/D regions, improving device performance and reliability. For example $Id_{sat}$ is improved by improved charge carrier mobility enabled by relaxed oxide filled STI structures. It will be appreciated that the relaxed oxide filled STI structure formation process may be advantageously used with other device technologies including substrates including strained Si, silicon on insulator (SOI), and SiGe as well as the formation of advanced MOSFET structures such as finFET devices.

Referring back to FIG. 1D, following blanket deposition of $SiO_2$ (STI oxide) e.g., 22 to backfill the STI trench 18 according to the preferred embodiments, a planarization process according to one of a dry etchback and CMP process is carried out where excess oxide above the trench level, including any hardmask layers above the SiN hardmask 14, is removed. For example, a portion of the STI oxide layer may be photolithographically patterned and partially removed by a conventional dry etchback process, followed by a conventional CMP process to remove any remaining excess oxide and hardmask layers above the SiN hardmask layer 14. For example, preferably, the CMP process is carried out at a removal rate of about 1000 Angstroms to about 5000 Angstroms/min and the dry etchback process is carried out at an etch rate of about 1000 to about 10000 Angstroms/min.

Figure 1E:
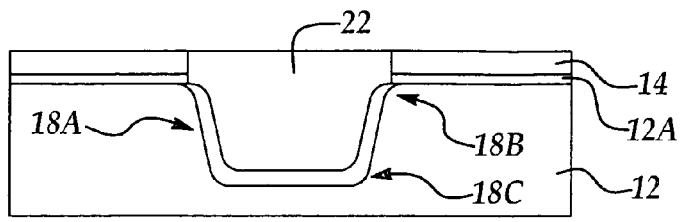
Figure 1F:
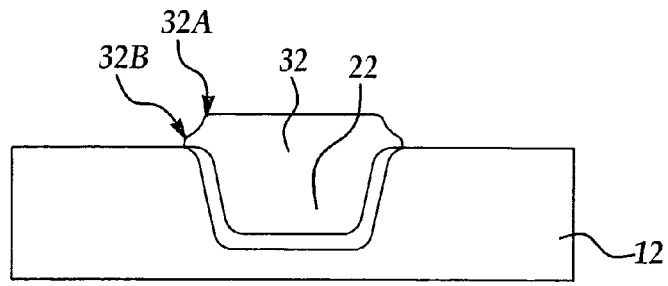

Referring to FIG. 1E, the SiN layer 14 is then removed by a conventional wet e.g., hot H₃PO₄, etching process or a dry SiN etchback process followed by a pad oxide layer 12A wet stripping process, for example using dilute HF, to leave a portion of the STI oxide layer e.g., 32 extending above the substrate 12 and having an inward edge e.g., 32A extending higher than an outward edge e.g., 32B.

Figure 3:
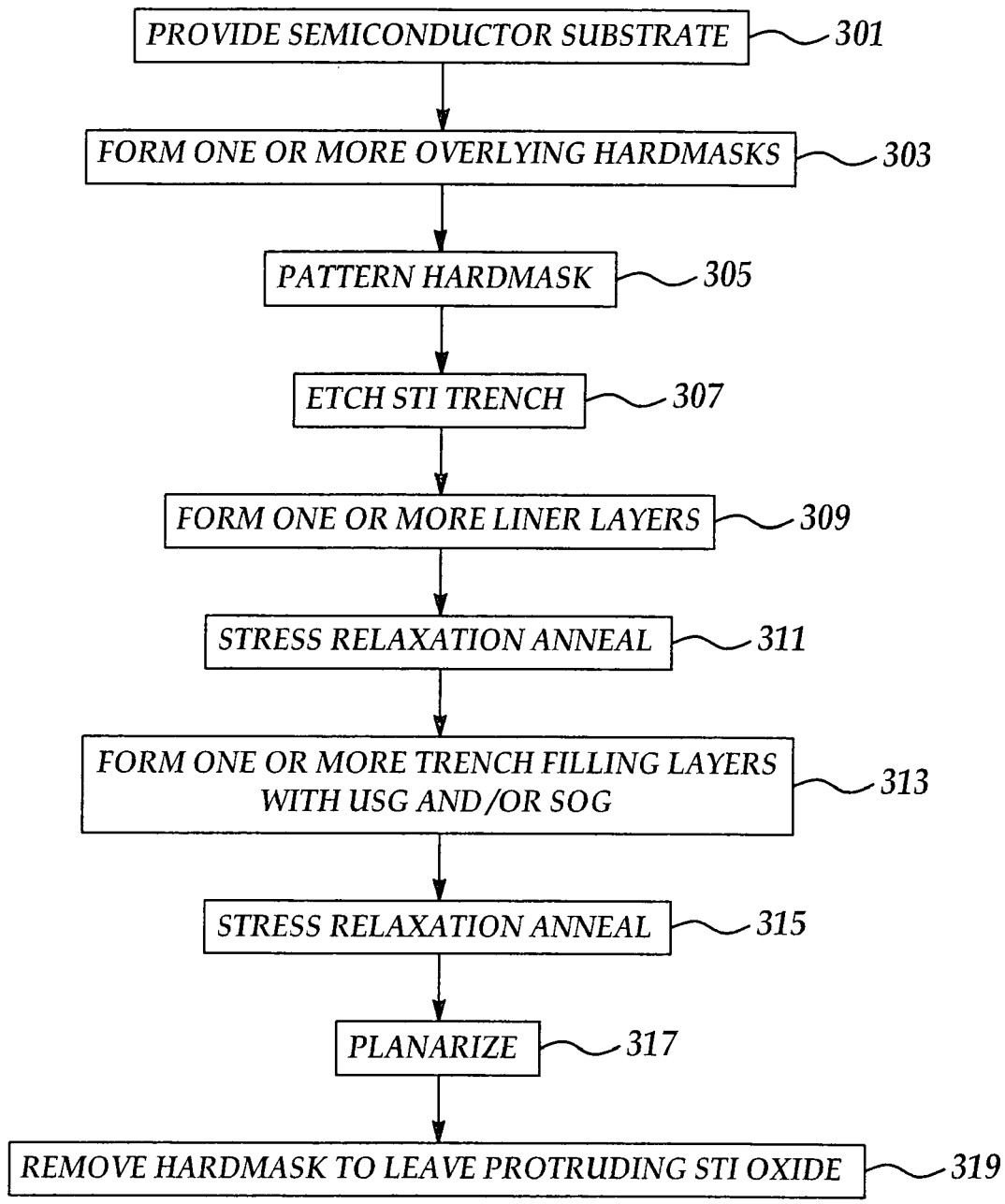
FIG. 3 is an exemplary process flow diagram including several embodiments of the present invention.

Referring to FIG. 3 is shown a process flow diagram including several embodiments of the present invention. In process 301 a semiconductor substrate is provided. In process 303, dielectric layers, including one or more hardmask layers is provided on the semiconductor substrate. In process 305, the one or more hardmask layers are patterned for etching STI trenches into the semiconductor substrate. In process 307, an STI trench feature is etched according to preferred embodiments. In process 309, one or more liner layers are formed to line the STI trench opening according to preferred embodiments. In process 311 an annealing process to relax stress in the liners is carried out. In process 313, one or more SiO₂ (USG and/or SOG) layers are deposited according to preferred embodiments. In process 315 an annealing process is carried out to relax stress in the STI oxide filling. In process 317, a planarization e.g., one of a CMP process and dry etch back process, is carried out to remove excess STI oxide and dielectric layers above the one or more e.g., SiN hardmask layer. In process 319, one of a wet or dry etchback process is carried out to remove the SiN hardmask layer leaving an upper portion of the STI oxide protruding higher than the semiconductor substrate level.

The preferred embodiments, aspects, and features of the invention having been described, it will be apparent to those skilled in the art that numerous variations, modifications, and substitutions may be made without departing from the spirit of the invention as disclosed and further claimed below.

What is claimed is:

1. A method of forming a stress relaxed shallow trench isolation (STI) structure to improve charge mobility of a MOSFET device comprising the steps of:
   providing a semiconductor substrate;
   forming a trench in the semiconductor substrate;
   forming a plurality of liner layers comprising an uppermost plurality of nitride liners selected from the group consisting of silicon nitride (SiN) and silicon oxynitride (SiON) to line the trench;
   then forming a plurality of trench filling oxide layers, said plurality of trench filing oxide layers is a spin-on glass (SOG) that comprises a precursor selected from the group consisting of organic and inorganic mixtures for forming cross-linked silicon oxide containing structures;
   wherein at least one stress relaxing thermal annealing step is carried out during and following formation of said plurality of trench filling oxide layers to form a trench filling substantially free of stress; and,
   removing excess trench filling oxide layers above the trench level.

2. The method of claim 1, further comprising forming at least one patterned hardmask layer selected from the group consisting of silicon nitride and silicon oxynitride over said substrate.

3. The method of claim 1, wherein the semiconductor substrate comprises material selected from the group consisting of silicon, silicon germanium, and gallium arsenide.

4. The method of claim 1, wherein the plurality of liner layers comprises a lowermost silicon oxide liner formed according to a method selected from the group consisting of thermal oxidation, LPCVD, and ALCVD.

5. The method of claim 1, wherein the step of forming the uppermost plurality of nitride liners comprises a process selected from the group consisting of treating and underlying thermal oxide liner with nitrogen, and depositing according to a CVD process.

6. The method of claim 1, wherein the precursor comprises a material selected from the group consisting of siloxanes, silanes, and polysesilquioxanes.

7. The method of claim 1, wherein the at least one stress relaxing thermal annealing step thermal annealing step is carried out following formation of each trench filling material layer to a desired filling level.

8. The method of claim 1, wherein the step of carrying out at least one stress relaxing thermal annealing step is carried out in an ambient selected from the group consisting of O₂ and N₂.

9. The method of claim 1, wherein the step of forming a trench comprises forming a trench comprising sidewalls having an angle with respect to a plane parallel to the substrate major surface of between about 80 degrees and about 89 degrees.

10. The method of claim 1, wherein the step of forming a trench comprises forming a trench comprising rounded top and/or bottom corners.

11. The method of claim 1, wherein the plurality of nitride liners comprises one of an SiN/SiON and SiON/SiN stack of layers.

12. A shallow trench isolation (STI) structure with reduced stress to improve charge mobility comprising:
   a semiconductor substrate;
   a trench formed through a thickness of the semiconductor substrate;
   a plurality of liner layers comprising an uppermost plurality of nitride liners selected from the group consisting of silicon nitride and silicon oxynitride lining the trench; and,
   a plurality of trench filling oxide layers on the uppermost plurality of nitride liners comprising an SOG layer and an uppermost USG layer, said plurality of trench filling oxide layers substantially free of stress in a direction substantially parallel or perpendicular to the semiconductor substrate major surface, said SOG layer comprises a precursor selected from the group consisting of siloxanes, silicates, and polysesilquioxanes.

13. The STI structure of claim 12, wherein the trench comprises sidewalls having an angle with respect to a plane parallel to the substrate major surface of between about 80 degrees and about 89 degrees.

14. The STI structure of claim 12, wherein the trench comprises rounded top and/or bottom corners.

15. The STI structure of claim 12, wherein the plurality of trench filling layers comprise a portion that extends above the semiconductor substrate surface.

16. The STI structure of claim 15, wherein the portion comprises an inward edge portion extending higher above the substrate surface compared to an outward edge portion.

17. The STI structure of claim 12, wherein the plurality of trench filling oxide layers comprises a lowermost SOG layer selected from the group consisting of organic and inorganic SOG layers, and an uppermost USG layer.

18. The STI structure of claim 12, wherein the plurality of trench filling oxide layers comprises a lowermost USG layer, an intervening SOG layer selected from the group consisting of organic and inorganic SOE layers, and an uppermost USG layer.

19. The STI structure of claim 12, wherein the plurality of trench filing oxide layers comprises a plurality of USG layers.

20. The STI structure of claim 12, wherein the plurality of trench filling oxide layers comprises a plurality of SOG layers selected from the group consisting of inorganic SOG layers and organic SOG layers.

21. The STI structure of claim 12, wherein the plurality of nitride liners is formed of one of an SiN/SiON and SiON/SiN stack.

22. The STI structure of claim 12, wherein the plurality of nitride liners is formed on a $SiO_2$ liner layer.

23. The STI structure of claim 12, wherein the plurality of liner layers is formed of a $SiO_2$/SiN/SiON stack.

24. The STI structure of claim 12, wherein the plurality of nitride liners comprises one of a SiN/SiON and SiON/SiN stack.

* * * * *